(12) United States Patent
Kort et al.

(10) Patent No.: US 8,986,946 B2
(45) Date of Patent: Mar. 24, 2015

(54) REAL-TIME METHOD FOR THE DETECTION OF VIABLE MICRO-ORGANISMS

(75) Inventors: Remco Kort, Amsterdam (NL); Frank Henri Johan Schuren, Veenendaal (NL); Roy Christiaan Montijn, Amersterdam (NL)

(73) Assignee: Nederlandse Organisatie Voor Toegepast-Natuurwetenschappelijk Onderzoek Tno, Delft (NL)

( * ) Notice: Subject to any disclaimer, the term of this patent is extended or adjusted under 35 U.S.C. 154(b) by 1268 days.

(21) Appl. No.: 12/809,566

(22) PCT Filed: Dec. 19, 2008

(86) PCT No.: PCT/NL2008/050828
§ 371 (c)(1),
(2), (4) Date: Oct. 27, 2011

(87) PCT Pub. No.: WO2009/082218
PCT Pub. Date: Jul. 2, 2009

(65) Prior Publication Data
US 2012/0122147 A1     May 17, 2012

(30) Foreign Application Priority Data

Dec. 20, 2007  (EP) ..................................... 07150271

(51) Int. Cl.
*C12Q 1/18*     (2006.01)
*C12Q 1/04*     (2006.01)
*G01N 21/64*    (2006.01)
*C12Q 1/06*     (2006.01)
*G01N 21/80*    (2006.01)

(52) U.S. Cl.
CPC .............. *C12Q 1/04* (2013.01); *G01N 21/6428* (2013.01); *G01N 21/80* (2013.01)
USPC .............................................. 435/32; 435/34

(58) Field of Classification Search
USPC ..................................................... 435/32, 34
See application file for complete search history.

(56) References Cited

U.S. PATENT DOCUMENTS

| 5,235,045 A | 8/1993 | Lewis et al. | |
|---|---|---|---|
| 6,589,761 B1 * | 7/2003 | Freadman et al. | 435/29 |
| 7,488,820 B2 * | 2/2009 | Lippard et al. | 540/474 |
| 2002/0037531 A1 * | 3/2002 | Brugge et al. | 435/7.1 |
| 2007/0166780 A1 | 7/2007 | Wilson | |

FOREIGN PATENT DOCUMENTS

| EP | 0 347 039 | 12/1989 |
|---|---|---|
| WO | WO-2005/052582 | 6/2005 |

OTHER PUBLICATIONS

Chang et al. 2004. A tautomeric zinc sensor for ratiometric fluorescence imaging: Application to nitric oxide-induced release of intracellular zinc. Proceedings of National Academy of Sciences of the United States of America (i.e., PNAS), vol. 101, No. 5, Feb. 3, 2004, pp. 1129-1134.*
Woodroofe et al., 2003. A Novel Two-Fluorophore Approach to Ratiometric Sensing of Zn2+. Journl of American Chemical Society, vol. 125, No. 38, pp. 11458-11459.*
Bracey et al. 1998. Determination of the intracellular pH (pHi) of growing cells of *Saccharomyces cerevisiae*: the effect of reduced-expression of the membrane H+-ATPase. Journal of Microbiological Methods, vol. 31, pp. 113-125.*
Bleve et al., Applied and Environmental Microbiology (2003) 69(7):4116-4122.
Garcia-Sanchob and Sanchez, Biochimica et Biophysica Acta (1978) 509:148-158.
Mishra et al., The Journal of Physical Chemistry (2005) 109(12):2746-2754.
Rao et al., Microbiology (2001) 147:1017-1024.
Rudi et al., Letters in Applied Microbiology (2005) 40(4):301-306.
International Search Report for PCT/NL2008/050828, mailed on Mar. 26, 2009, 4 pages.

* cited by examiner

*Primary Examiner* — Jon P Weber
*Assistant Examiner* — Kailash C Srivastava
(74) *Attorney, Agent, or Firm* — Morrison & Foerster LLP

(57) ABSTRACT

The invention relates to a method for real-time detection of viable microorganisms comprising: a. addition of a cell-permeable, phototautomeric compound to a micro-organism or other living cell; and b. measuring the fluorescent emission of said phototautomeric compound. Preferably the phototautomeric compound is salicylic acid, 2-hydroxy-1-naphtoic acid or 1-hydroxy-2-naphtoic acid. Further, the assay can he used to assess the antibiotic effect of a test compound. This test can be used as a high—throughput screening for compounds with antibiotic activity. Also part of the invention is the use of a cell permeable phototautomeric compound in a method for determining the viability of micro-organisms and for assessing the antibiotic effect of a test compound.

7 Claims, 12 Drawing Sheets

Figure 1:
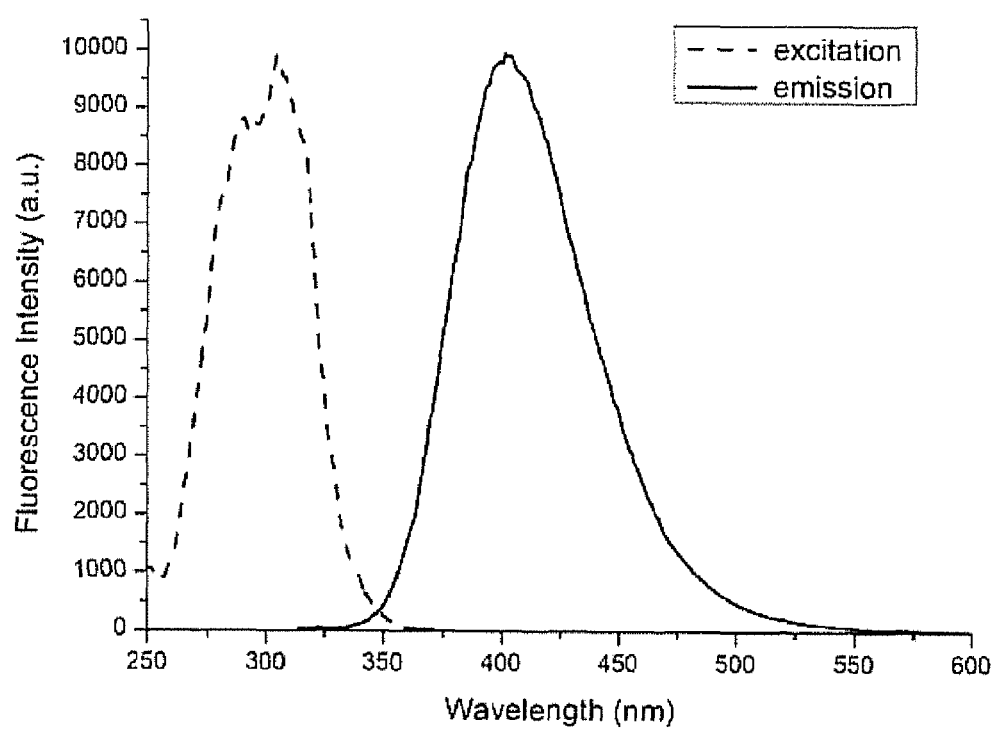

| code | name | structure | excitation maximum (nm) | emission maximum (nm) | pKa | ratio pH7,5/1 or pH7/2* | uptake bacteria | uptake yeast |
|---|---|---|---|---|---|---|---|---|
| V1 | salicylic acid | 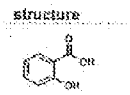 | 295 | 405 | 2.9 | 122 | + | + |
| V2 | 4-amino salicylic acid | 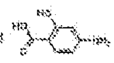 | 295 (265) | 400 | 2.2 (3.5) | 22 (74) | + | - |
| V3 | 5-amino salicylic acid | 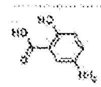 | 335 | 495 | 5.8 | 331 | - | - |
| V4 | 5-hydroxy salicylic acid (gentisic acid) | 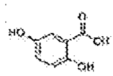 | 322 | 448 | 2.9 | 77 | + | - |
| V5 | 4-hydroxy salicylic acid | 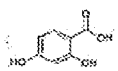 | 290 | 395 | 3.0 | 52 | + | - |
| V6 | 1-hydroxy-2-naphtoic acid | 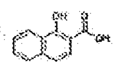 | 340 | 420 | 3.0 | 3 | + | + |
| V7 | 3-amino-2-naphtoic acid | 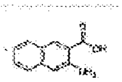 | 360 (265) | 470 | 4.5 | 88 (42) | + | + |
| V8 | o-hydroxycinnamic acid (o-coumarine zuur) | 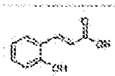 | 326 (360) | 500 | 5.5 (>9) | 38 (408) | + | - |
| V9 | S350729 2-Hydroxy-dibenzofuran-3-carboxylic acid | 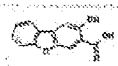 | 340 (300) | 450 | 2.3 | 4.3 (0.7) | + | + |
| V10 | 6-Amino-1,3-dimethyl-2-oxo-2,3-dihydro-1H-benzoimidazole-5-carboxylic acid | 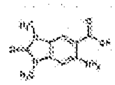 | 241 | 396 | n.d. | 1.4* | - | + |
| V11 | 5-(2-Ethyl-butyrylamino)-2-hydroxy-benzoic acid | 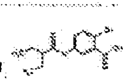 | 311 | 426 | n.d. | 23.0* | + | - |
| V12 | 2-Hydroxy-5-[(tetrahydro-furan-2-carbonyl)-amino]-benzoic acid | 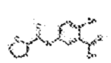 | 307 | 417 | n.d. | 17* | + | - |
| V13 | 7-Amino-2,3-dihydro-benzo[1,4]dioxine-6-carboxylic acid | 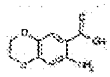 | 323 | 401 | n.d. | 358* | + | - |
| V14 | 2-Hydroxy-5-tetrazol-1-yl-benzoic acid | 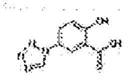 | 296 | 395 | n.d. | 5* | + | + |

Figure 6

REAL-TIME METHOD FOR THE DETECTION OF VIABLE MICRO-ORGANISMS

CROSS-REFERENCE TO RELATED APPLICATIONS

This application is the national phase of PCT application PCT/NL2008/050828 having an international filing date of 19 Dec. 2008, which claims benefit of European patent application No. 07150271.0 filed 20 Dec. 2007. The contents of the above patent applications are incorporated by reference herein in their entirety.

The invention relates to the field of microbiology, more particular to thescreening of samples for viable micro-organisms or spores. In a special embodiment, the invention relates to the field of antibiotic compounds, more especially to testing compounds for their antibiotic activity.

Knowledge on the presence of viable micro-organisms plays a role in many food and environment issues. For food and drinking water safety and conservation treatments it is important to know whether (pathogenic) micro-organisms are present in the samples and whether these are viable or not. This not only holds true for pathogenic micro-organisms. Also for the increasingly popular probiotic food supplements it is important to know whether the beneficial micro-organisms therein are viable or not.

Further, for testing the contamination of surfaces and/or the efficacy of disinfectants, e.g. in or on medical diagnostic devices and/or kitchen machinery, it is important to determine the presence of any viable micro-organisms. A system for assaying the presence of viable micro-organisms can also be suitably used to screen for new antibiotic compounds.

Antibiotic compounds have been a topic of interest since the discovery of the antibiotic properties of penicillin by Fleming. A variety of methods are employed for measuring the susceptibility of bacteria or other micro-organisms to antibiotic compounds. Viability in bacteria is frequently equated with the ability to form colonies on solid growth medium or to proliferate in nutrient-containing solution. Thus, conventionally, plate counting (e.g. Li, R. C. et al., 1996, Antimicrob. Agents Chemother. 40, 1751-1753; Virta, M. et al, 1994, Antimicrob. Agents Chemother. 36, 303-315) has been the method of use for testing antibiotic activity. However, such methods do not provide results on a real-time basis. Another frequently used in vitro technique is the microdilution method (Amsterdam, D., 1996, in: Lorian, V. (ed) Antibiotics in Laboratory medicine, $4^{th}$ ed. Wilkins and Wilkins, Baltimore, Md., USA, p. 52-111), in which target bacteria are distributed into a microtiter plate, followed by varying concentrations of the compound to be tested. After a suitable incubation period (e.g. overnight) the plate is evaluated photometrically for bacterial growth, and the effects of the compound are assessed.

Thus, while most of the present methods reveal the possibly antibiotic effects of a compound against target bacteria after prolonged (overnight) incubation, the need for faster analyses is evident. Real-time assays for the detection of viable micro-organisms, and thus for the assessment of biocidal activity have recently been described, e.g. by Lehtinen, J. et al., 2006, J. Microbiol. Meth. 66:381-389. In some cases, such an assay is based on the differential staining of the microbial cells with fluorescent dyes, such as SYTOX Green Nucleic Acid Stain (obtainable from Molecular Probes, Eugene, Oreg., USA) as described in Roth, B. L. et al., 1997, Appl. Environm. Microbiol., 63(6): 2421-2431, and a two dye based (SYTO9 and propidium iodide) system in the LIVE/DEAD BacLight bacterial viability kit (L7012, Molecular probes, Leiden, the Netherlands) as described in Nohynek, L. J. et al., 2006, Nutrition and Cancer, 54(1): 18-32. Yet, there is still need for alternative methods.

SUMMARY OF THE INVENTION

The inventors now have found an alternative, rapid and cost-efficient method for real-time viability assay of micro-organisms. The assay comprises addition of a cell-permeable, phototautomeric compound to a micro-organism or other living cell, followed by measuring the fluorescent emission of said compound. Preferably the phototautomeric compound is salicylic acid, 2-hydroxy-1-naphtoic acid or 1-hydroxy-2-naphtoic acid. Further, the assay can be used to assess the antibiotic effect of a test compound. This test can be used as a high-throughput screening for compounds with antibiotic activity.

Also part of the invention is the use of a cell permeable phototautomeric compound in a method for determining the viability of micro-organisms and for assessing the antibiotic effect of a test compound.

LEGENDS TO THE FIGURES

FIG. 1 shows the excitation (dashed line) and emission spectra (solid line) of 2 mM salicylate in 100 mM potassium phosphate buffer at pH 7. Excitation and emission spectra were recorded in a Tecan microplate fluorometer at 402-nm emission and 290-nm excitation, respectively. Fluorescence intensity is expressed in arbitrary units (a.u.).

Figure 2:
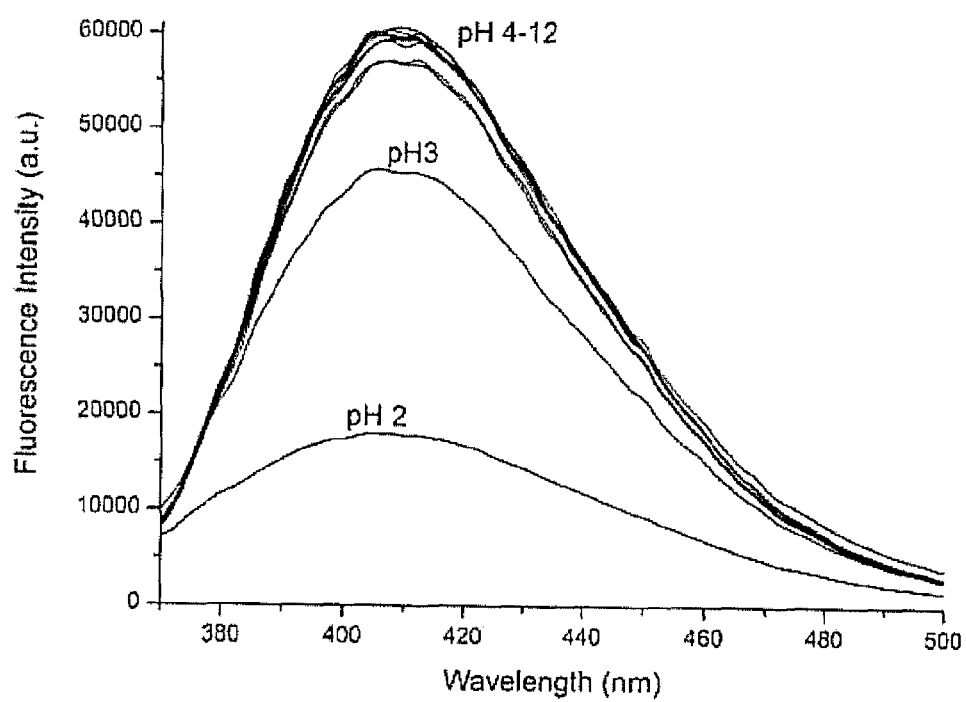

FIG. 2 shows the fluorescence emission spectra of 2 mM salicylic acid in 100 mM potassium phosphate buffer ranging in pH value from 2 to 12. Emission spectra were recorded in a Tecan microplate fluorometer at 290-nm excitation. Fluorescence intensity is expressed in arbitrary units (a.u.).

Figure 3:
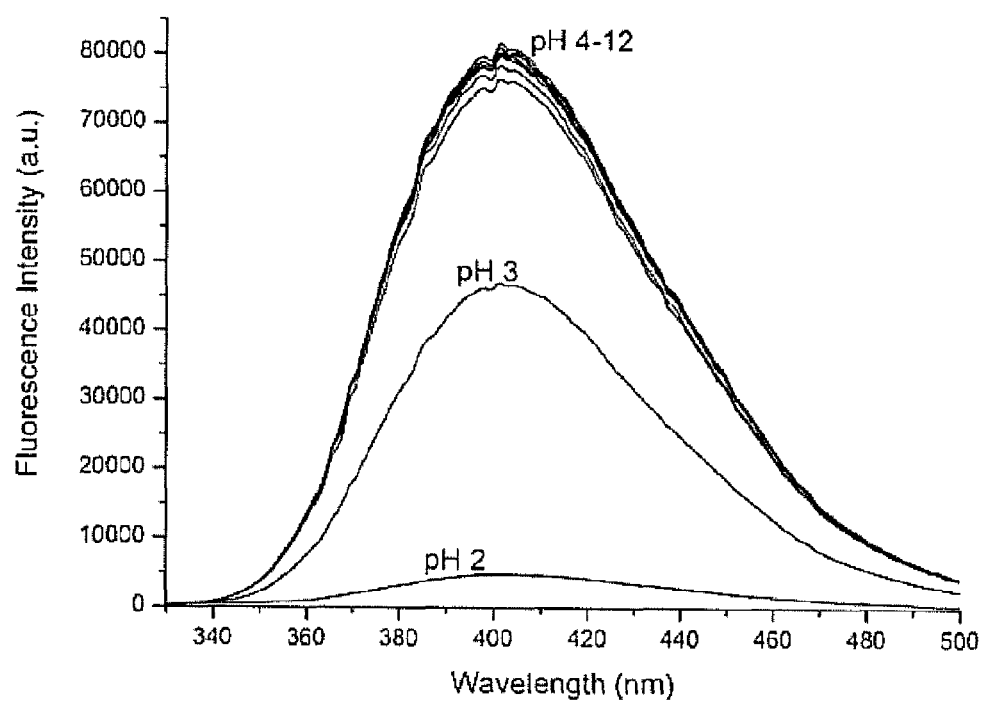

FIG. 3 shows the fluorescence emission spectra of 20 μM 1-hydroxy-2-naphtoic acid in 100 mM potassium phosphate buffer ranging in pH value from 2 to 12. Emission spectra were recorded in a Tecan microplate fluorometer at 340-nm excitation. Fluorescence intensity is expressed in arbitrary units (a.u.).

Figure 4:
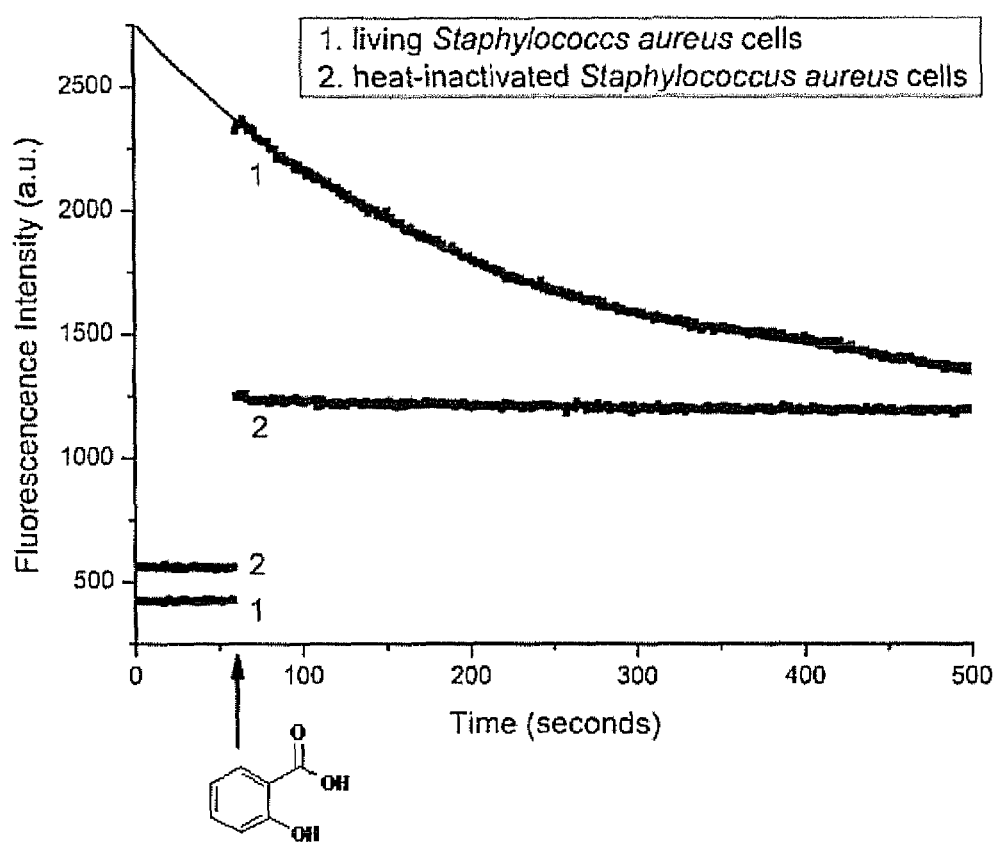

FIG. 4 shows real-time monitoring of cell viability in 100-μl cell suspensions of viable *Staphylococcus aureus* strain ATCC 6538 (trace 1) and nonviable *Staphylococcus aureus* (heat-inactivated for 5 minutes at 95° C.; trace 2). A solution of 100 μl containing 2 mM salicylic acid, 100 mM potassium phosphate buffer pH 2, was added at t=60 seconds, as indicated by the arrow. Trace 1 (viable cells): The black squares indicate the background signal in the absence of salicylic acid (0-60 seconds), the rise in fluorescence by the rapid transfer of salicylic acid from the extracellular to the intracellular medium (60-65 seconds) and the loss of membrane integrity or cell viability (from 65 seconds). The process fits a function with exponential decay y (t)=1507 $e^{200/t}$+1254 (solid line). Trace 2 (nonviable cells): The black squares indicate the background signal in the absence of salicylic acid (0-60 seconds) and the rise in fluorescence from residual salicylate anions present at pH 2 (from 60 seconds).

Figure 5:
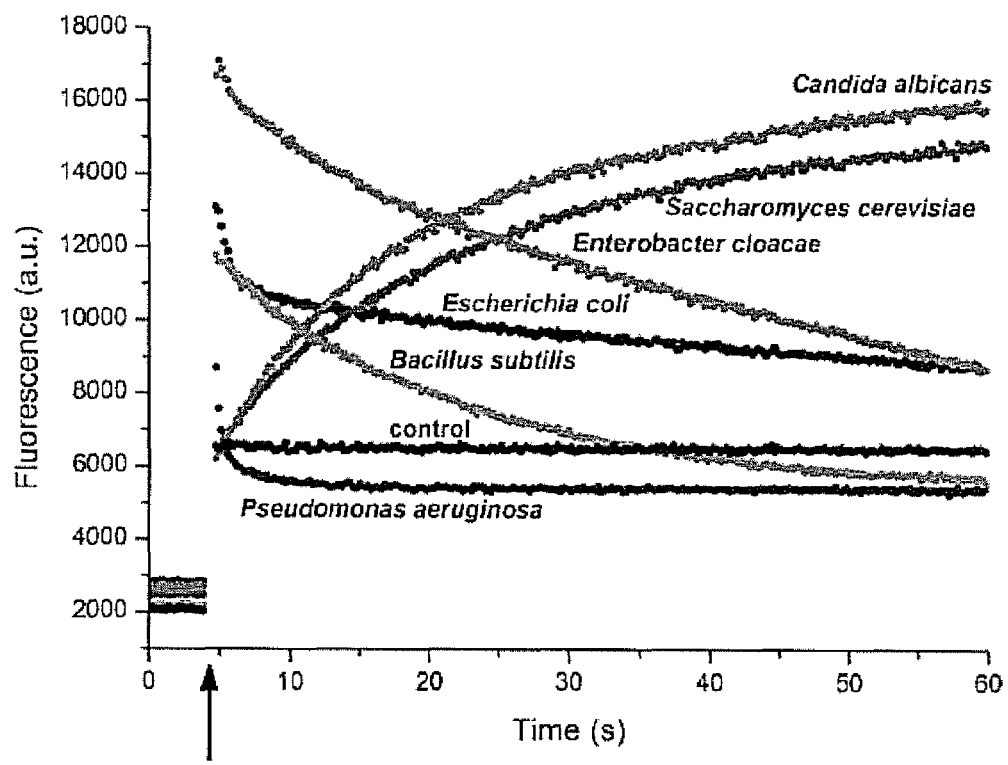

FIG. 5 shows real-time monitoring of cell viability in 100 μl of a suspension of stationary cells of *Escherichia coli* ($OD_{600}$=1.786), *Saccharomyces cerevisiae* ($OD_{600}$=1.291), *Pseudomonas aeruginosa* ($OD_{600}$=1.438), *Candida albicans* ($OD_{600}$=1.958), *Enterobacter cloacae* ($OD_{600}$=1.867), *Bacillus subtilis* $OD_{600}$=1.434) and a control of physiological salt solution (peptone, 0.9% NaCl). Uptake kinetics of salicylic acid and membrane integrity were followed after injection of 100 µl 2 mM salicylic acid, 100 mM potassium phosphate buffer, pH 2 at t=4 seconds, as indicated by the arrow.

FIG. 6 shows an overview of fluorescent compounds which can be used for real-time monitoring of cell viability. A solution of 100 µl containing 50 µM compound in 100 mM potassium phosphate buffer pH 7 is used for recording the excitation and emission wavelengths in a Tecan microplate fluorometer. The ratio of emission intensity at pH 7.5 and 1 as well as the ratio of emission intensity at pH 7 and 2 (indicated by the asterisk) was recorded with 100 µl solution containing 50 µM compound in 100 mM potassium phosphate buffer pH 2 or 7 in a Tecan microplate fluorometer at optimal excitation wavelength. Uptake of compounds by viable and nonviable (heat-inactivated for 5 minutes at 95° C.) *Staphylococcus aureus* ATCC 6538 and *Sachromyces serervisiae* ATCC 9763 cells is real-time monitored in a Tecan microplate fluorometer at optimal excitation and emission wavelengths. A solution of 50 µM compound in 100 mM potassium phosphate buffer pH2 was added to 100 µl cell suspensions at t=20 seconds, uptake of compound was monitored for 180 seconds.

Figure 7:
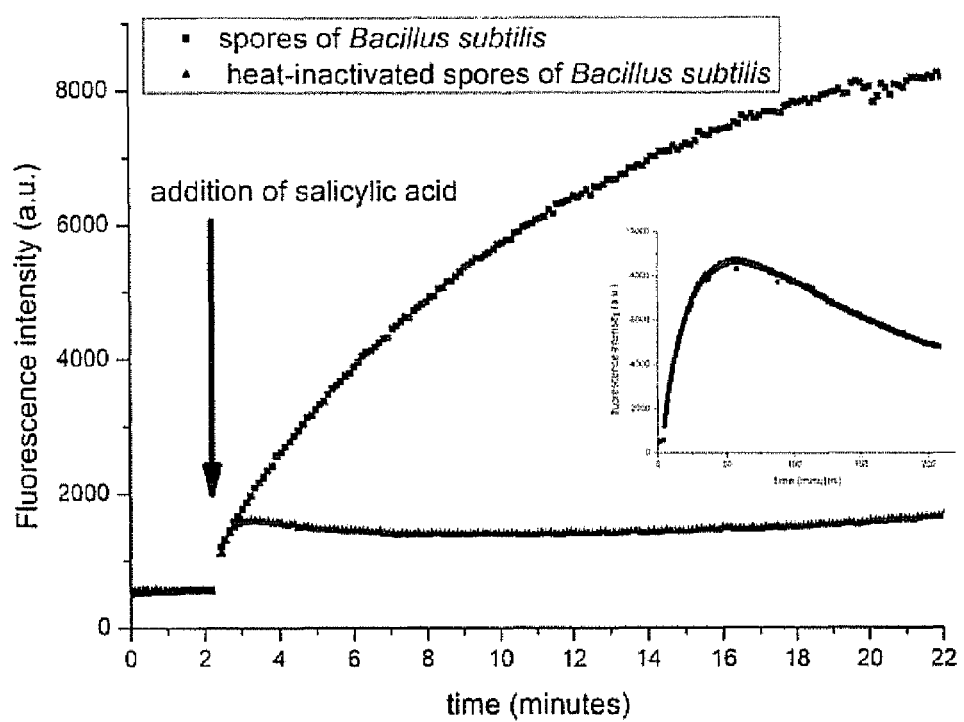

FIG. 7 shows real-time monitoring of cell viability of viable Bacillus subtilis A163 spores and nonviable *Bacillus subtilis* spores (heat-inactivated for 20 minutes at 121° C.). A solution of 100 µl containing 2 mM salicylic acid in 100 mM potassium phosphate buffer pH 2, was added to 100 µl spore suspensions at t=2,5 minutes, as indicated by the arrow. Measurements before t=2,5 minutes indicate the background signal in the absence of salicylic acid (0-2,5 minutes). The rise in fluorescence (2,5-22 minutes) by the black squares (viable spores) indicates the transfer of salicylic acid from the extracellular to the intracellular medium of spores. The inserted plot indicates the decrease in fluorescence signal for a longer period of time (220 min). The black triangles (nonviable spores) indicate the background signal in the absence of salicylic acid (0-60 seconds) and the rise in fluorescence from residual salicylate anions present at pH 2 (2,5-22 minutes).

Figure 8:
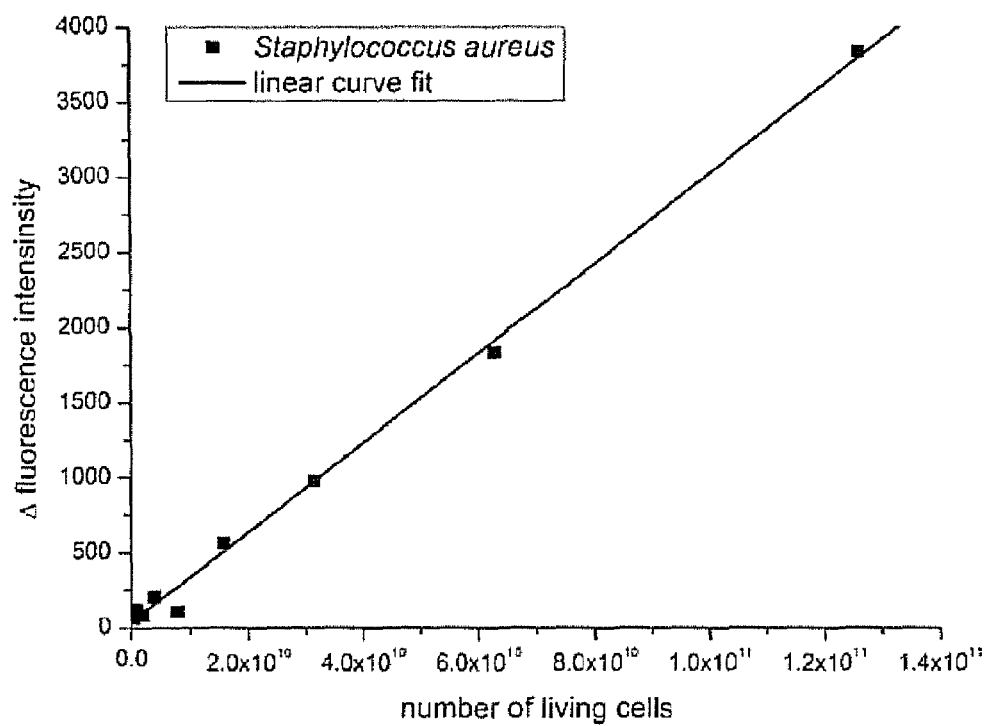

FIG. 8 shows the relation between the change in fluorescence intensity and number of living cells. A solution of 100 µl containing 2 mM salicylic acid, 100 mM potassium phosphate buffer pH 2, was added to dilutions of 100 µl cell suspensions of *Staphylococcus aureus* ATCC 6538 at t=20 seconds (cell density was measured at 600 nm and cell counts were determined for reference in a hemocytometer). Fluorescence signal was real-time monitored in a Tecan microplate fluorometer from 0 to 300 seconds. The change in fluorescence was determined by using fluorescence signal on t=21 seconds and average fluorescence of t=290-300 seconds.

Figure 9:
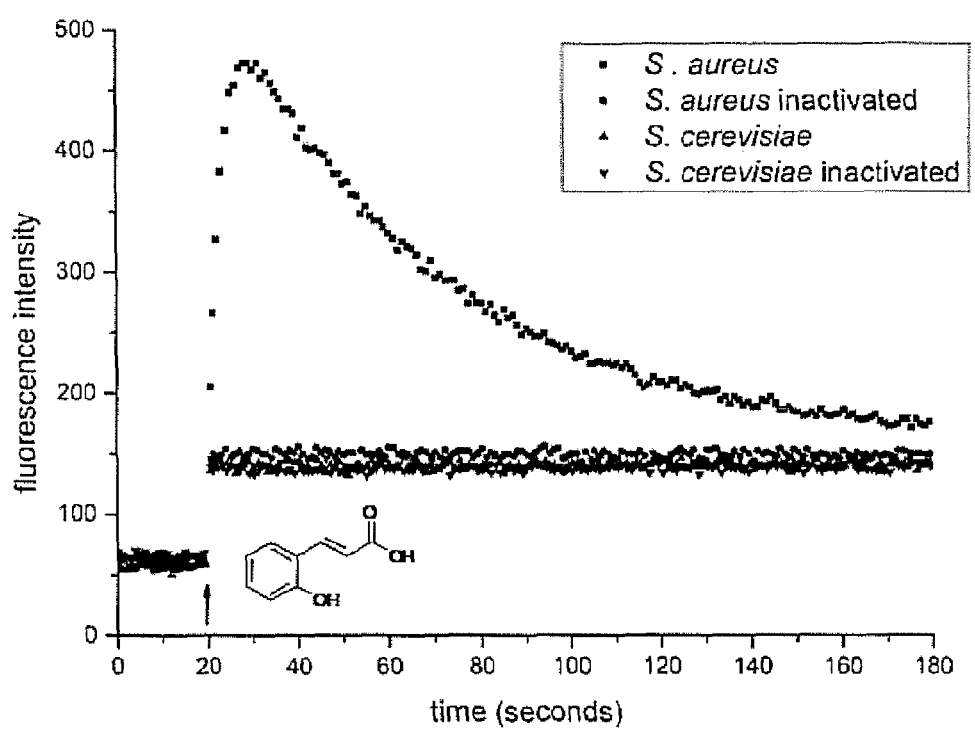

FIG. 9 shows real-time monitoring of cell viability in 100 µl cell suspensions of viable and nonviable (heat-inactivated for 5 minutes at 95° C.) *Staphylococcus aureus* ATCC 6538 and Saccharomyces cerevisiae ATCC 9763 cells. A solution of 100 µl containing 50 µM o-hydroxycinnamic acid, 100 mM potassium phosphate buffer pH 2, was added at t=20 seconds, as indicated by the arrow. Rise in fluorescence (t=20-30 seconds) was only observed for viable *Staphylococcus aureus* cells.

Figure 10:
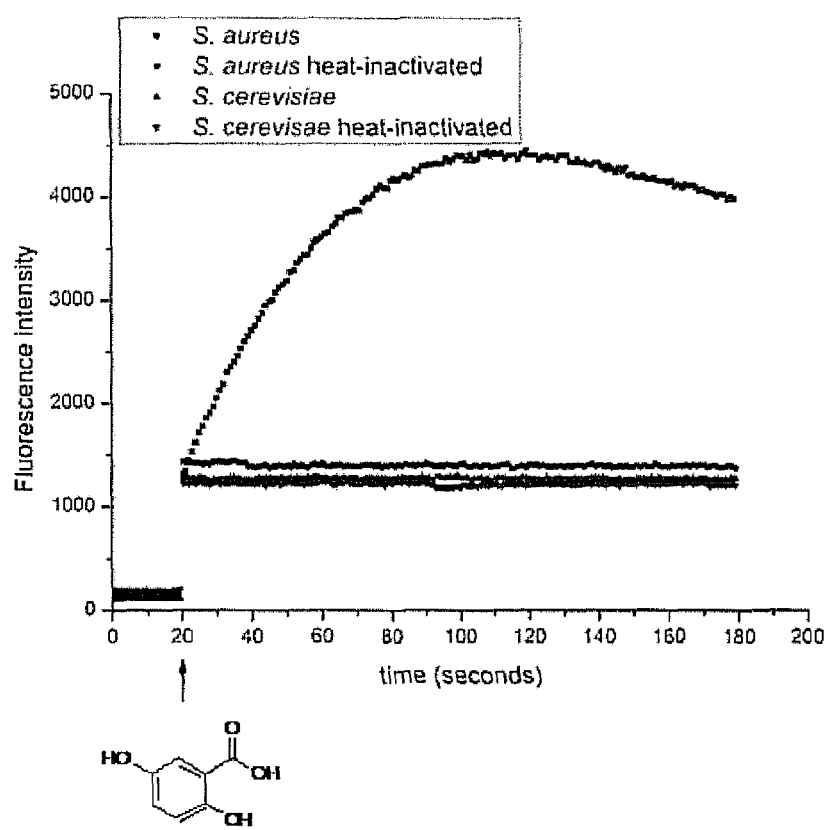

FIG. 10. shows real-time monitoring of cell viability as described in FIG. 9 for compound gentisic acid (2,5-dihydroxybenzoic acid; 5-hydroxy-salicylic acid). Rise in fluorescence was only observed for viable Staphylococcus aureus cells.

Figure 11:
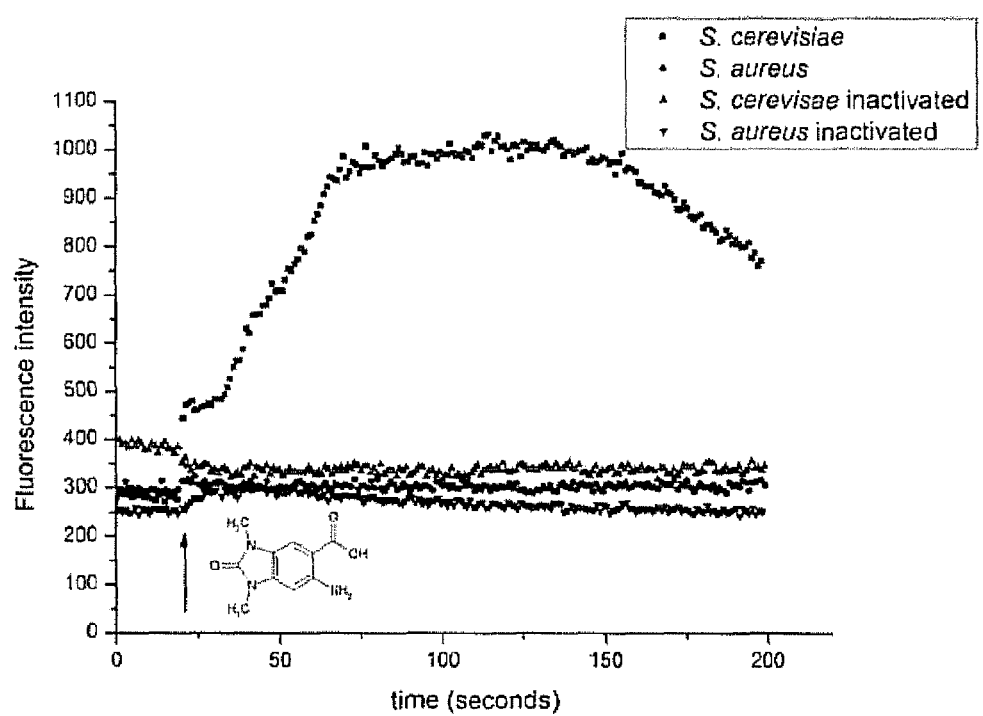

FIG. 11. shows real-time monitoring of cell viability as described in FIG. 9 for compound 6-amino-1,3-dimethyl-2-oxo-2,3-dihydro-1H-benzoimidazole-5-carboxylic acid. Rise in fluorescence was only observed for viable *Saccharomyces cereuisiae* cells.

Figure 12:
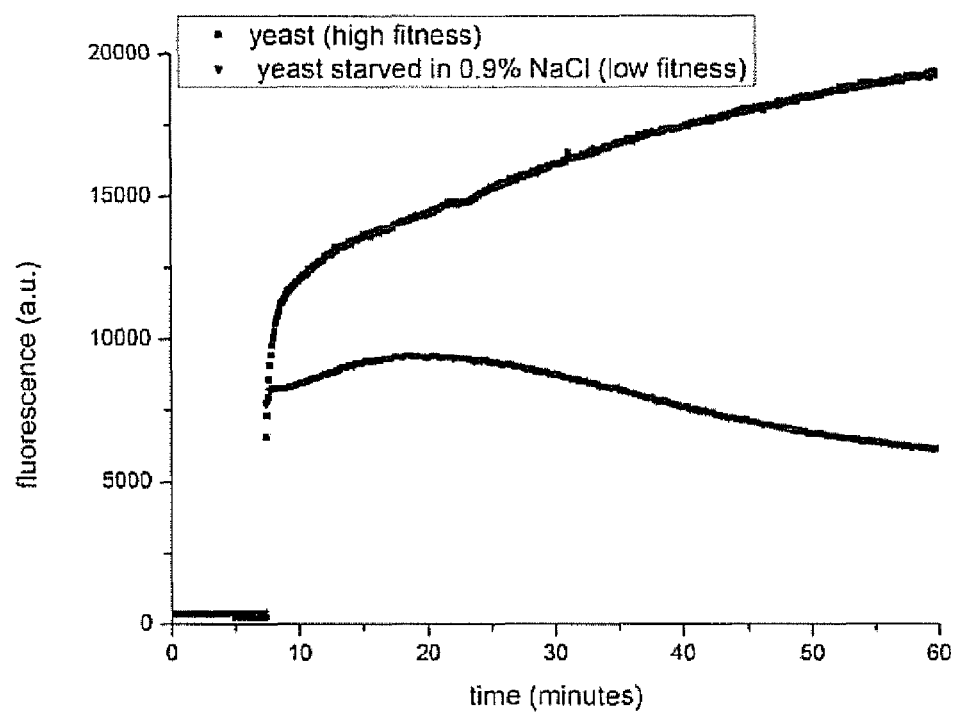

FIG. 12. shows that the salicylic acid probe assay (as described in FIG. 4) can be used to assess the fitness of microbial cells. A fresh culture of *Saccharomyces cerevisiae* (squares) was compared to a culture of *Saccharomyces cerevisiae* (triangles), which was pre-incubated under starvation conditions for 6 hours in 0.9% NaCl.

DETAILED DESCRIPTION

Phototautomerism refers to a phenomenon that occurs in certain molecules containing at least two ionizing functional groups and involves photoexcitation to the lowest excited singlet state, which results in the "simultaneous" loss of a proton from one group and gain of a proton by another. Thus, phototautomerism occurs without any net ionization. Phototautomerism is frequently observed in polyfunctional molecules containing at least one electron acceptor group (which becomes more basic in the excited state) and one electron donor group (which becomes more acidic in the excited state). If the electron acceptor group becomes sufficiently basic and the electron donor group sufficiently acidic upon excitation, the acceptor group may become protonated and the donor group dissociated. This is usually observed as an anomalously large Stokes shift of the fluorescence, in other words the fluorescence band lies at much longer wavelengths than would be anticipated on the basis of the electronic structure of the neutral molecule. In so-called phototautomeric compounds or phototautomers, the electron acceptor and donor groups are usually situated ortho or peri to one another on an aromatic ring, with an intramolecular hydrogen bond bridging the two functional groups (e.g. salicylic acid and 1-hydroxy-2-naphtoic acid, respectively). In some instances, however, intramolecular hydrogen bonding occurs between aryl substituent groups and acidic or basic groups on side chains. Upon excitation, the hydrogen atom belonging to the electron donor group is transferred predominantly or entirely to the electron acceptor (ref: Stephen G Schulman. Acid-Base Chemistry of Excited Singlet States in *Modern Fluorescence Spectroscopy, Part* 2. Edited by E. L. Wehry, Heyden London, 1976. Page 263-266)

Intramolecular phototautomerism in salicylic acid was first demonstrated by Weller, who noted that the fluorescence of salicylic acid occurred at much longer wavelength (~410 nm) than that of o-anisic acid (~340 nm), the latter containing a methoxy group rather than a hydroxy group, so that phototautomersim is not possible (ref: A. H. Weller, Fast reactions of excited molecules, Prog. React. Kinet. 1 (1961), pp. 187-214). Various fluorescence emitting species of salicylic acid have been identified. In concentrated sulfuric acid, emission from the cation is observed, whereas in concentrated KOH solution, the dianion is the emitting species. In alcohols, e.g. methanol, both the zwitterion and monoanion show emission, whereas in water only the monoanion shows emission (ref Joshi H. C.; Mishra H.; Tripathi H. B (1997) Photophysics and photochemistry of salicylic acid revisited. Journal of Photochemistry and Photobiology A: Chemistry, 105:15-20). As the fluorescence emission in water is determined by the presence of the singly charged anion species, the intensity of the emission spectrum dramatically increases upon decreasing the acidity from pH 2 to pH 4 in line with the pKa value of 2.97 for the aromatic carboxyl group in salicylic acid (ref: C. B. Amphlett, G. E. Adams and B. D. Michael, Pulse radiolysis studies of deaerated aqueous salicylate solutions, Adv. Chem. Ser. 81 (1968), pp. 231-250), as demonstrated in FIGS. 2 and 3 for the phototautomeric compounds: salicylic acid and 1-hydroxy-2-naphtoic acid, respectively. Thus, as the pH interval from 2 to 4 is traversed, the fluorescence changes to that of the excited singly charged anion ionized at the phenolic group, the latter being formed only by the direct excitation and rapid intramolecular phototautomerization of the singly charged ground-state anion (ionized at the carboxyl group).

Compounds that are useful as phototautomeric compounds in the present invention are the above mentioned salicyclic acid, 2-hydroxy-1-naphtoic acid, 1-hydroxy-2-naphtoic acid, quinolines, isoflavones, uracil and derivatives thereof. A list of specific, preferred compounds is given in FIG. 6.

Using this difference in fluorescence emission, it is possible to discriminate between the phototautomeric compound being in conditions of low pH or being in conditions of high pH. A condition of low pH is herein defined as a pH of the solution, in which the phototautomeric compound is dissolved, in which the protonated or neutral acid is responsible for the fluorescence (preferably low emission), whereas a condition of high pH is defined as the pH of the solution, in which the phototautomeric compound is dissolved, in which the singly charged anion is responsible for the fluorescence (preferably high emission).

Although one is inclined to think that the pivotal point for the shift in fluorescence state is the pKa value of the compound, this is not exactly true. It is therefore better to define a new parameter, the pKf, which is the −log [H+] concentration of the medium in which the phototautomeric compound is dissolved below which point the compound is in another fluorescent phase than above. This pKf value can easily be obtained for each compound by continuously decreasing or increasing the pH of a solution of the compound and to determine at which point the compound starts or stops to emit fluorescence. Generally, the pKf will be in the neighbourhood of the pKa of the compound.

The intracellular pH in living microbial cells varies between 4.5 and 8. If pH 4.5-8 is defined as a "high pH" and a phototautomeric compound in a "low pH" solution is added to the microbial cells, then upon excitation the fluorescence emission will differ between the individual phototautomeric molecules that remain outside the cell and those that have been transferred into the intracellular medium. If microbial cells start to leak or burst open, the acidic medium solution can enter the cell, which acidifies and wherein thus the phototautomeric compound will eventually be in a "low pH" condition. The process of transfer (either actively or passively) of the compound in the cell and death of the cell through membrane-leakage can advantageously be followed by real-time fluorescence measurements. In this way the fluorescence measurements give an indication on the presence of living (i.e. viable) cells and the deterioration rate of the cells rate in the acidic medium.

In the prior art, use of fluorescent dyes that cannot permeate microbial membranes and thus are able to contact cell material of leaky (dead or dying) microbial cells, but not of living microbial cells has been applied for discriminating between living and dead microbial cells. One such dye is e.g. SYTOX Green Nucleic Acid Stain, which is able to bind to nucleic acid (both DNA and RNA). The discrimination in the DEAD/LIVE stain is based on two dyes: SYTO9 which permeates living cells and propidium iodide which does not. Accordingly, the latter dye only stains dead cells.

The disadvantage of having to use two fluorescent dyes is thus solved by the present invention, which uses the pH dependent fluorescence characteristics of phototautomeric compounds, such as salicylic acid, 1-hydroxy-2-naphtoic acid and 2-hydroxy-1-naphtoic acid and compounds presented in FIG. 6, to discriminate between living and dead cells It is known that cell membranes are affected by weak organic acids, such as the phototautomeric compounds described above. For lactic acid an effect has been described on bacterial cells (see Alakomi, H.-L., et al., 2000, Appl. Environment. Microbiol. 66(5): 2001-2005), while for salicylic acid and dihydroxy benzoic acid an effect has been described on human and murine leukaemia cells (Feix, J.B. et al., 1994, Cancer Res. 54:3474-3478). The exact effect of the compounds is unclear, and it seems that different acids would have different effects. For instance, lactic acid is said to be a potent membrane disrupting agent (even stronger than hydrochloric acid), while salicylic acid is said to change membrane potentials. Further, both lactic acid and salicylic acid have a biocidal effect.

Salicylic acid, also known as 2-hydroxybenzoic acid, one of several beta hydroxy acids (compare to AHA), is a key ingredient in many skin-care products for the treatment of acne, psoriasis, calluses, corns, keratosis pilaris, and warts. It works by causing the cells of the epidermis to slough off more readily, preventing pores from clogging up, and allowing room for new cell growth. Because of its effect on skin cells, salicylic acid is used in several shampoos used to treat dandruff. Salicylic acid is also used as an active ingredient in gels which remove verrucas (plantar warts). Use of concentrated solutions of salicylic acid may cause hyperpigmentation on unpretreated skin for those with darker skin types (Fitzpatrick phototypes IV, V, VI), as well as with the lack of use of a broad spectrum sunblock. [4][5]

The medicinal properties of salicylate, mainly for fever relief, have been known since ancient times, and it was used as an anti-inflammatory drug.[6]

Although toxic in large quantities, salicylic acid is used as a food preservative and antiseptic in toothpaste. For some people with salicylate sensitivity even these small doses can be harmful. Sodium salicylate is a useful phosphor in the vacuum ultraviolet with nearly flat quantum efficiency for wavelengths between 10 to 100 nm. [7] It fluoresces in the blue at 420 nm. It is easily prepared on a clean surface by spraying a saturated solution of the salt in methanol followed by evaporation.

In a stationary culture of S. aureus, which is incubated in the presence of 100 mM potassium phosphate buffer, 2 mM salicylic acid (pH 2) salicylic acid is rapidly taken up by the bacteria (within seconds) where after the bacteria gradually loose their membrane integrity (see FIG. 3).

Salicylic acid is characterised in that it has a difference in fluorescence emission intensity (at 402 nm) at the maximal wavelength for excitation (290 nm) at different pHs. As indicated above, this difference in signal intensity can be advantageously used in combination with the above mentioned effects of these acids on the membrane of micro-organisms. Cells that take up the salicylic acid will slowly acidify and eventually obtain a pH which is equal to the pH of the medium. Thus, by monitoring the fluorescence emission, living cells can be identified and the process of acidification, resulting in cell death, can be monitored. It appears that this acidification process, at least in S. aureus, has a time constant of 0.005 $s^{-1}$. (FIG. 3). However, as can be seen in FIG. 4 this varies from micro-organism to micro-organism, where it is believed that the acidification process is faster in Gram-negative micro-organisms, such as E. coli, than in Gram-positive organisms, such as S. aureus. Strikingly, S. cerevisiae shows an increase in fluorescence in the first 500 seconds, which is in line with the higher acid tolerance of this organism. Further, in S. cerevisiae there is a relatively slow rise in fluorescence in contrast to the rapid rise in bacteria, showing that the cell membrane of *S. cerevisiae* is less-permeable to salicylic acid.

In the prior art (Garcia-Sancho, J and Sanchez, A., 1978, Biochim. Biophys. Act., 509:148-158) salicyclic acid has been used to estimate the pH inside the (bacterial) cell. This was achieved by assessing the distribution of radioactively labeled salicylic acid between the intracellular and the extracellular phase. However, since no pH conditions under pH 4.3 were tested, the authors did not recognize the phenomenon that is the subject of the present invention which would enable to test for the viability of the micro-organism.

First, the present method can be used to assess the presence of viable micro-organisms. In this respect, the medium in which the assay is performed can be selected from the group of air, an aqueous solution, emulsion or dispersion, a culture medium, soil, a dairy product and a food product. Thus, such a method can be used for the testing of food, air and water contamination, and contamination of surfaces (such as from diagnostic or therapeutic devices, surgical invasive and non-invasive instruments or apparatuses, and surfaces on which food is stored or prepared). In such an assay, a surface is sprayed with a solution of 100 mM phospate buffer, pH 2, 1 mM salicylic acid or any other combination of an acidic buffer and a phototautomeric compound; during the spray process the surface is exposed to UV-light and a camera monitors the surface (note that most cameras are insensitive to UV-light and very sensitive to BLUE light (400-450 nm). In this way any microbial contamination (any living cell keeping a neutral pH) will start to fluoresce. Note that this method will be much more sensitive than the assays discussed before; a microplate reader is a sub-optimal platform for UV-excitation in terms of light source and transprancy of microplates It has also now been found that the variety in phototautomeric compounds that can achieve this effect, which are characterized by their fluorescence at different wavelengths, also can accommodate in making a distinction in the type of micro-organism that is detected. For instance there are phototautomeric compounds which are taken up by both bacteria and yeast (such as salicylic acid, 1-hydroxy-2-napthoic acid, 3-amino-2-napthoic acid and S350729), while other compounds are hardly taken up by yeast (such as 4-hydroxy salicylic acid, 4-amino salicylic acid, 5-amino salicylic acid and o-hydroxycinnamic acid). It is also contemplated that there will be compounds that are especially useful in Gram-negative bacteria or Gram-positive bacteria. Use of a combination of these compounds in one assay, whereby detection takes place at two or more wavelengths, can thus already give an indication of the type of micro-organism that is detected.

Further, the method according to the invention is applicable to determine the viability of micro-organisms. A great advantage is that the effects of the addition of a phototautomeric compound to a culture of micro-organisms can be measured real-time, and that a typical test run only requires several minutes of testing. Next, since the measuring of fluorescence is a commonly used optical assay method, it is possible to use standard equipment. This facilitates testing of multiple concentrations of micro-organism and acid, even in duplicate or multiplicate, to achieve reliable results. Further, the standard read-out systems accommodate various types of phototautomeric compounds, media and buffers that can be used in the method of the invention. For testing the viability of a micro-organism an appropriate sample is e.g. placed in a well of a microtiter plate, fluorescence is measured at 402 nm (to determine the background level) and, while continuing the fluorescence measurements, a solution of the phototautomeric compound at the discriminatory high or low pH condition is added to the well. Appropriate controls would be a well with no added phototautomeric compound, a well comprising viable cells and a well comprising dead cells. The amount of phototautomeric compound needed for a useful assay can be detected through testing various concentrations, but will normally vary from 0.01 mM to 10 mM, and the resulting pH of the solution should not be close to pH 7. The desired pH depends on the phototautomeric compound used. A pH of about 2 is preferred for salicylic acid and is reached with a solution of 1-2 mM salicylic acid in a 100 mM potassium phosphate buffer.

In principle all varieties of micro-organisms can be used in the assay, such as bacteria, fungi, algae, cell cultures of animal and plant cells, etc. Preferably bacterial cells are tested. It has also proven possible to determine the viability of bacterial and fungal spores (see experimental part). Although the timeframe of an assay in which the viability of spores is assessed in much larger than the timeframe in which the viability of bacteria or other cellular organisms is tested (minutes versus seconds, respectively), such an assay should be considered as a major improvement over the currently known assays.

Using the above described assay it is also possible to assay the antibiotic effect of chemical or biological compounds by adding them to the micro-organism and testing the viability of the cells which have undergone such a treatment. The microtiter plate design of the test allows for the testing of series of compounds or various concentrations of one compound. In the latter case, it is especially suitable to establish an $IC_{50}$. Other variations may be the time that the micro-organisms are exposed to the compound to be tested and changes in the conditions of exposure (i.e. temperature, pH, osmolarity of the buffer, etc.). Herewith a cost efficient and versatile assay for the detection of antibiotic compounds is provided. Also, the present method enables high-throughput screening on antibiotic activity. Such a high-throughput screening is feasible since multiple compounds and/or multiple concentrations of a compound can be tested simultaneously and since the actual test time is very short (one to a few minutes), and since the test does only require standard laboratory equipment.

The assay methods of the invention can also be used to measure the fitness of the micro-organisms. As can be seen from the figures (e.g. FIG. 4, 5) the micro-organisms that are contacted with the phototautomeric compound will slowly die as a result from leakage of the acidic medium into the bacterial cell, causing a gentle slope in the fluorescence over time. The rate with which the cells die is a measure for the viability of the cells, and thus the slope of the fluorescence emission over time, which reflects the rate death of the micro-organism, thus is a good measure for the determination of the fitness of the bacteria (see also FIG. 12). Such a determination is important when micro-organisms are cultured, used in probiotics or used as starter cultures for food fermentations, such as cheese production, sausage production, beer and wine production and for bacterial treatments of plant pathogens.

The methods of the invention are now illustrated in the following examples, which should not be construed as limiting the general concept of the invention.

Example 1

Measurement of fluorescence excitation of salicylic acid (SA), 2-hydroxy-1-naphtoic acid (2H-1NA) and 1-hydroxy-2-naphtoic acid (1H-2NA). The excitation spectra were monitored in the microplate fluorometer Tecan Infinite M200 (Tecan Benelux, Giessen, Germany) in a polystyrene 96-well, black, flat-bottom microtiter plate, with a volume of 392 µl/well (Greiner Bio-One Inc). The standard experimental settings included a fluorescence top reading at room temperature in a volume of 100 µl; integration time 20 µs; number of reads 25; wavelength step size 1 nm; wavelength range of 230-380 nm; excitation bandwidth 5 nm (range 1: 230-295 nm) and 9 nm (range 2: 296-850 nm); emission bandwidth 20 nm; lag time 0 µs; settle time 1 ms; manual gain of 50. Salicylic acid was obtained from Fluka Chemica and used at a concentration of 2 mM; 2H-1NA and 1H-2NA were obtained from Sigma Aldrich Inc. and used at concentrations of 200 µM and 20 respectively. Measurements were carried out with SA, 2H-1NA and 1H-2-NA dissolved in 100 mM potassium phosphate buffer, pH 7. The excitation spectrum of SA was recorded at an emission wavelength of 402 nm, the spectra for 2H-1NA and 1H-2NA were recorded at an emission wavelength of 412 nm.

Example 2

Measurement of the fluorescence emission of SA, 2H-1NA and 1H-2-NA at various pHs. The emission spectra were monitored in the microplate fluorometer specified above. The standard experimental settings included a fluorescence top reading at room temperature in a volume of 100 µl as specified above. Emission measurements for SA, 2H-1NA and 1H-2NA were carried out in 100 mM potassium phosphate buffers, ranging from pH 2 to pH 12. Emission spectra for SA were recorded at a concentration of 2 mM, wavelength range of 330-500 nm, manual gain of 70 and excitation wavelength of 290 nm. Emission spectra for 2H-1NA and 1H-2NA were recorded at concentrations of 200 µM and 20 µM, respectively, wavelength range 360-500 nm, manual gain of 80 and excitation wavelength of 340 nm.

Example 3

Typical real-time viability assay. *Staphylococcus aureus* strain ATCC 6538 is cultured overnight at 100 RPM at 37° C. in 10-ml of a rich trypticase soy broth (TSB) medium. A culture volume of 5 ml is centrifuged at 2000 RPM for 10 min and resuspended in 2 ml of physiological salt solution (peptone, 0.9% NaCl) followed by an OD600 measurement. A culture suspension of 1 ml is heat-inactivated by incubation at 95° C. for 5 min. (nonviable control cell suspension). A volume of 100 µl of a viable and a nonviable cell suspension is pipetted in separate wells of a polystyrene 96-well, flat-bottom microtiter plate. Subsequently, fluorescence emission kinetics (excitation wavelength 290 nm; emission wavelength 402 nm) are monitored for 500 seconds with a time interval of 200 ms, number of reads 5. At the time point of 60 seconds, 100 µl of 2 mM salicylic acid, 100 mM potassium phosphate buffer, pH 2 is injected in the wells containing the viable and the nonviable cell suspensions. The rapid rise in fluorescence on a sub-second time scale (<200 ms) corresponds to the rapid transfer of salicylic acid from the extracellular to the intracellular medium. Hereafter, the fluorescence signal decays on a minute time-scale as a result of the loss of membrane integrity or cell viability. Hence, the difference of fluorescence between the time point at 60.2 seconds and 500 seconds is approximately proportional to the number of viable cells in the cell suspension. The control sample containing the nonviable cells shows a rise in fluorescence at the time point of 60 seconds resulting from residual salicylate anions present at pH 2. From 60.2 seconds the signal will remain constant as the membrane is permeable in nonviable cells allowing quenching of fluorescence by acidification of the intracellular environment.

Example 4

A calibration curve for the number of viable *Staphylococcus aureus* cells. A *Staphylococcus aureus* strain ATCC 6538 is cultured overnight at 100 RPM at 37° C. in 10-ml of a rich trypticase soy broth (TSB) medium. A culture volume of 5 ml is centrifuged at 2000 RPM for 10 min and resuspended in 2 ml of physiological salt solution (peptone, 0.9% NaCl) followed by an $OD_{600}$ measurement. The bacterial suspension is further diluted in physiological salt by factors of 2, 4, 16, 32, 64, 128, 256, 512, 1024 and 2048. A volume of 100 µl of each of the cell suspension dilutions is pipetted in separate wells of a polystyrene 96-well, flat-bottom microtiter plate. Subsequently, fluorescence emission kinetics is followed as specified above. Subsequently, the difference of fluorescence between the first time point after SA injection (at 60.2 seconds) and final time point (500 seconds) is plotted as a function of the number of viable cells in the cell suspension to obtain a calibration curve.

Example 5

Real-time viability assay for various micro-organisms. Bacterial and yeast strains were cultured overnight at 37° C. at 100 RPM in 10-ml of a rich trypticase soy broth (TSB) medium. A culture volume of 5 ml is centrifuged at 2000 RPM for 10 min and resuspended in 2 ml of physiological salt solution (peptone, 0.9% NaCl) followed by an $OD_{600}$ measurement. The yeast strains include *Candida albicans* ATCC 10231, *Saccharomyces cereuisiae* ATCC9763 and the bacterial strains include A *Staphylococcus aureus* strain ATCC 6538, *Enterobacter cloacae* LMG 2783, *Escherichia coli* ATCC 10536, *Bacillus subtilis* DSM618 and *Pseudomonas aeruginosa* ATCC27853. The assay is carried out as specified above for *Staphylococcus aureus*. Note that the yeast (and other fungal) strains accumulate SA, 2H-1NA and 1H-2NA relatively slowly, while there is no decay of fluorescent signal, showing that their membranes remain intact under the conditions used. Accordingly, quantification of the number of viable cells of the yeast and other fungal strains should occur on the basis of increase of fluorescence over the measured period of time.

The invention claimed is:
1. A method for real-time detection of viable living cells comprising
  a. adding a cell-permeable, phototautomeric compound to a medium to be tested for the presence or absence of living cells, in which medium the phototautomeric compound does not emit fluorescence;
  wherein the fluorescence of said phototautomeric compound is high at an intracellular pH, as compared to low emission at the pH of the medium in which said phototautomeric compound is supplied; and
  b. measuring any fluorescent emission of said phototautomeric compound;
  wherein the presence of fluorescent emission indicates the presence of living cells in the medium and the absence of fluorescence emission indicates the absence of living cells in the medium.
2. The method of claim 1, wherein the phototautomeric compound is salicylic acid,
  2-hydroxy-1-naphtoic acid,
  1-hydroxy-2-naphtoic acid,
  4-amino salicylic acid, gentisic acid,
4-hydroxy salicylic acid,
3-amino-2naphtoic acid,
o-hydroxycinnamic acid,
2-hydroxy-dibenzofuran-3-carboxylic acid (S350729),
6-amino-1,3-dimethyl-2-oxo-2,3-dihydro-1H-benzoimidazole-5-carboxylic acid,
5-(2-ethyl-butyrylamino)-2-hydroxy-benzoic acid,
2-hydroxy-5-[(tertrahydro-furan-2-carbonyl)-amino]-benzoic acid,
7-amino-2,3-dihydro-benzo[1,4]dioxine-6-carboxylic acid or
2-hydroxy-5-tetrazol-1-yl-benzoic acid.

3. The method of claim 1, wherein the living cells are microbial cells.

4. The method of claim 1, wherein the medium is air, an aqueous solution, emulsion or dispersion, a culture medium, soil, a dairy product or a food product.

5. The method of claim 1 wherein the living cells are yeast cells.

6. The method of claim 1 wherein the living cells are bacteria.

7. The method of claim 1 wherein the living cells are spores.

* * * * *